(12) United States Patent
Bao et al.

(10) Patent No.: US 10,811,125 B2
(45) Date of Patent: Oct. 20, 2020

(54) COGNITIVE FRAMEWORK TO IDENTIFY MEDICAL CASE SAFETY REPORTS IN FREE FORM TEXT

(71) Applicant: International Business Machines Corporation, Armonk, NY (US)

(72) Inventors: Shenghua Bao, San Jose, CA (US); Meenakshi Nagarajan, San Jose, CA (US); Cartic Ramakrishnan, San Jose, CA (US); John C. Unterholzner, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 281 days.

(21) Appl. No.: 15/681,722

(22) Filed: Aug. 21, 2017

(65) Prior Publication Data
US 2019/0057191 A1    Feb. 21, 2019

(51) Int. Cl.
*G16H 15/00*    (2018.01)
*G16H 10/60*    (2018.01)
(Continued)

(52) U.S. Cl.
CPC ............ *G16H 15/00* (2018.01); *G06F 16/35* (2019.01); *G16H 10/60* (2018.01); *G16H 70/40* (2018.01)

(58) Field of Classification Search
CPC ........ G16H 15/00; G16H 10/20; G16H 50/20; G16H 50/70; G06F 19/328; G06F 19/00; G06F 16/35; G06F 16/36
(Continued)

(56) References Cited

U.S. PATENT DOCUMENTS 8,645,424 B2    2/2014  Miller
2009/0070103 A1*  3/2009  Beggelman ............. G06F 17/27
                                                           704/9
(Continued)

OTHER PUBLICATIONS

Noren, GN et al.; "Duplicate Detection in Adverse Drug Reaction Surveillance"; Data Mining and Knowledge Discovery, vol. 14, No. 3, pp. 305-328, Jun. 2007.
(Continued)

*Primary Examiner* — Hiep V Nguyen
(74) *Attorney, Agent, or Firm* — Will Stock; SVL IPLaw Edell, Shapriro & Finnan, LLC (57) ABSTRACT

A method, a computing system and a computer program product are provided. A computing system identifies elements within a collection of medical documents. The elements include patients, adverse events and medical drugs. The medical documents are analyzed by the computer system to determine associations between the identified medical drugs and corresponding identified adverse events. The identified elements and the determined associations may be encoded as features by the computing system. The computing system identifies portions of the medical documents as containing the identified elements and the determined associations. The computing system generates a classification model based at least on the encoded features associated with the identified portions for identifying medical case safety reports within medical documents. The classification model is applied to a new document to determine a classification of the new document with respect to a medical case safety report.

21 Claims, 5 Drawing Sheets

(51) Int. Cl.
*G06F 16/35* (2019.01)
*G16H 70/40* (2018.01)

(58) Field of Classification Search
USPC .......................................................... 705/2, 3
See application file for complete search history.

(56) References Cited

U.S. PATENT DOCUMENTS

| | | | | |
|---|---|---|---|---|
| 2013/0073571 | A1* | 3/2013 | Coulet | G16B 50/00 707/755 |
| 2015/0234921 | A1 | 8/2015 | Li | |
| 2016/0048655 | A1* | 2/2016 | Maitra | G16H 50/70 705/3 |

OTHER PUBLICATIONS

Anonymously; "A Method and System for Detecting Cognitive Change of an Individual by Monitoring Communication Patterns"; http://ip.com/IPCOM/000242934D; Sep. 1, 2015.

Anonymously; "Cognitive Feedback Analysis to Proactively Trigger Automatic System Modifications and User Actions"; http://ip.com/IPCOM/000247630D; Sep. 21, 2016.

Anonymously; "Cognitive Reporting of Doctor-Patient Consultation"; http://ip.com/IPCOM/000247997D; Oct. 14, 2016.

Eltyeb, S. et al.; "Pattern-Based System to Detect the Adverse Drug Effect Sentences"; Journal of Theoretical and Applied Information Technology, vol. 71, No. 1, pp. 137-143, Jan. 2015.

Tregunno et al., "Performance of Probabilistic Method to Detect Duplicate Individual Case Safety Reports", Drug Saf (2014) 37: 249. doi:10.1007/s40264-014-0146-y. Springer, Drug Safety, Apr. 2014, vol. 37, Issue 4, 4 pages.

Rochefort et al., "Accuracy of using automated methods for detecting adverse events from electronic health record data: a reasearch protocol", Implementation Science, 2015, 9 pages.

Polepalli Ramesh, Balaji, "Adverse Drug Event Detection, Causality Inference, Patient Communication and Translational Research", University of Wisconsin Milwaukee, UWM Digital Commons, Theses and Dissertations, Paper 512, May 2014, 227 pages.

Harpaz et al., "Text Mining for Adverse Drug Events: the Promise, Challenges, and State of the Art", Drug Saf. Oct. 2014; 37(10): 777-790. doi:10.1007/s40264-014-0218-z. NIH Public Access, Author Manuscript, Oct. 2015, 25 pages.

* cited by examiner

Title: A case of fatal acute liver failure in a 68 year old female treated with erlotinib for lung adenocarcinoma
Dr. Cyrielle 12234 Jardin cyrielle.jardin@chru-lille.fr MD 1, Dr. Arnaud 12235 Desplechin desplechin.arnaud@ghicl.net MD 3, Dr. MIE 12236 Delourme julie.delourme@chru-lille.fr MD 2, Dr. ZErn 12254 D'Halluin xavier.dhalluin@chru-lille.fr MD 2, Prof. Dr Arnaud 15686 Scherpereel arnaud.scherpereel@chru-lille.fr MD 2, Prof. Dr ean-Jacques- 15693 Lafitte jean-jacques.lafitte@chru-lille.fr MD 2 and Dr. 2= 15703 Cortot alexis.cortot@chru-lille.fr MD 2. 1 Service de Pneumo-Immuno-Allergologie, Hopital Calmette, CHRU, Lille, France ; 2 Service de Pneumologie et Oncologie Thoracique, Hopital Calmette, CHRU, Lille, France and 3 Service d'Onco-Hematologie, Hopital Saint Vincent de Paul, Lille, France .

Body: A 68 year old female with a history of levothyroxine-substituted hypothyroidism was diagnosed with metastatic lung adenocarcinoma. She was treated with 3 courses of a platinum-based chemotherapy as first-line treatment and docetaxel as second-line treatment. She received daily injections of fondaparinux because of a recent pulmonary embolism. Despite these treatments, the patient developed lymphangitic carcinomatosis and brain metastasis, and erlotinib was initiated. 18 days later, she was admitted at the emergency room for vomiting and dehydration. Clinical findings included mild abdominal pain in the upper right quadrant. Blood tests showed elevated liver enzymes (AST 7900 IU/L (N<40), ALT 9200 IU/L (N<40) and acute liver failure (32% PT, 13% factor V). Paracetamol blood level was negative, as well as HIV, EBV, VZV, CMV and hepatitis A, B and C tests. Abdominal ultrasound showed no obstruction on the biliary tract, no portal thrombosis. The patient rapidly developed metabolic encephalopathy, leading to her death within 18 hours after admission. Careful interrogation of her relatives and general practitioner did not reveal medications other than erlotinib, levothyroxine and fondaparinux. Previous liver blood tests during chemotherapy were normal. Acute liver failure due to erlotinib was then considered as the probable cause of death.

FIG.6

COGNITIVE FRAMEWORK TO IDENTIFY MEDICAL CASE SAFETY REPORTS IN FREE FORM TEXT

BACKGROUND

Present invention embodiments are related to systems, methods and computer program products for Medical Case Safety Report detection from any type of textual data in a document.

Medical case safety reports such as, for example, individual case safety reports (ICSRs) for a pharmaceutical company, are generated for drug-related adverse events found in a case document. Detection of a medical case safety report includes: identifying whether the case document mentions a patient taking a drug of the pharmaceutical company; determining whether the document mentions at least one adverse event; and determining whether the document mentions a reporter who initiated the case document. Pharmaceutical companies often include organizational process information (i.e., specific meta-rules or conditions that must be satisfied) regarding the detection of a medical case safety report. Cases may come from a variety of sources including, but not limited to, call centers, solicited reports, medical literature, clinical trials, legal documents, social media documents, scientific literature and spontaneous reports by healthcare professionals. Because pharmaceutical companies collect statistics regarding adverse events caused by medical drugs in their drug portfolios, correctly identifying medical case safety reports is important with respect to maintaining the statistics.

Currently, detection of medical case safety reports such as, for example, ICSRs, is a labor-intensive and time-consuming process that includes drug safety experts carefully reading and reviewing cases to determine whether the cases are potential ICSRs. Technological assistance may be provided to the drug safety experts by use of keyword-based techniques. Recently, machine learning and natural language processing have been used to find adverse events in case documents. One existing pharmacovigilance system efficiently and automatically processes medical records to extract information and relationships contained therein, and perform a preliminary assessment regarding a medical or clinical judgment. The system may automatically generate reports, which are validated by trained clinicians and medical experts. Machine learning was dismissed for use in the pharmacovigilance system because it was believed to be too expensive and considered to be poorly performing. The pharmacovigilance system includes a natural language processing pipeline and utilizes a rules engine to assess and confirm a presence of a causal link between consumption of a drug and an adverse event experienced by a patient.

SUMMARY

In an embodiment, a computer-implemented method is provided for monitoring medical documents. Elements within a collection of medical documents are identified. The elements include patients, adverse events and medical drugs. The medical documents are analyzed to determine associations between the identified medical drugs and corresponding identified adverse events. The identified elements and the determined associations may be encoded as features. Portions of the medical documents are identified as containing the identified elements and the determined associations. A classification model is generated based at least on the encoded features associated with the identified portions of the medical documents to identify medical case safety reports within the medical documents. The classification model may be applied to a new document to determine a classification of the new document with respect to a medical case safety report. The embodiments transform a pharmacovigilance process by: reducing an amount of time to process a case; drawing an expert's attention to focal sentences that contain evidence for a medical case safety report; identifying elements of a medical case safety report and reducing errors regarding identification of drugs or adverse events.

In some embodiments, patients may be identified based on semantic lexicon expansion of an initial group of terms, reporters of the adverse events may be identified based on named entity recognition techniques, and medical drugs may be identified based on natural language processing and knowledge borrowing techniques. Associations between the identified medical drugs and the corresponding identified adverse events may be determined based on a natural language processing dependency parse tree. In some embodiments, features may be encoded and may include at least one organizational meta-rule, thereby making these embodiments more flexible with respect to specific features or meta-rules employed by an organization.

BRIEF DESCRIPTION OF THE DRAWINGS

Generally, like reference numerals in the various figures are utilized to designate like components.

FIG. 6 shows an example of focal sentences identified in a document.

DETAILED DESCRIPTION

Present invention embodiments include methods, systems and computer program products for detecting a medical case safety report within documents. A computing system may identify one or more elements within a collection of medical documents. The elements may include a reference to a patient, an adverse event, a reporter of the adverse event, and a medical drug. The computing system may analyze the medical documents to determine associations indicating a respective identified medical drug causing a corresponding identified adverse event regarding a corresponding patient. The identified elements, the determined associations, and organizational meta-rules may be encoded by the computing system as features. Portions of the medical documents containing the identified elements and the determined associations may be identified as focal sentences. The computing system may generate a classification model based at least on the encoded features associated with the identified portions of the medical documents to identify medical case safety reports within the medical documents concerning medical drugs. The computing system may apply the classification model to a new document to determine a classification of the new document as a valid medical case safety report or an invalid medical case safety report.

Figure 1:
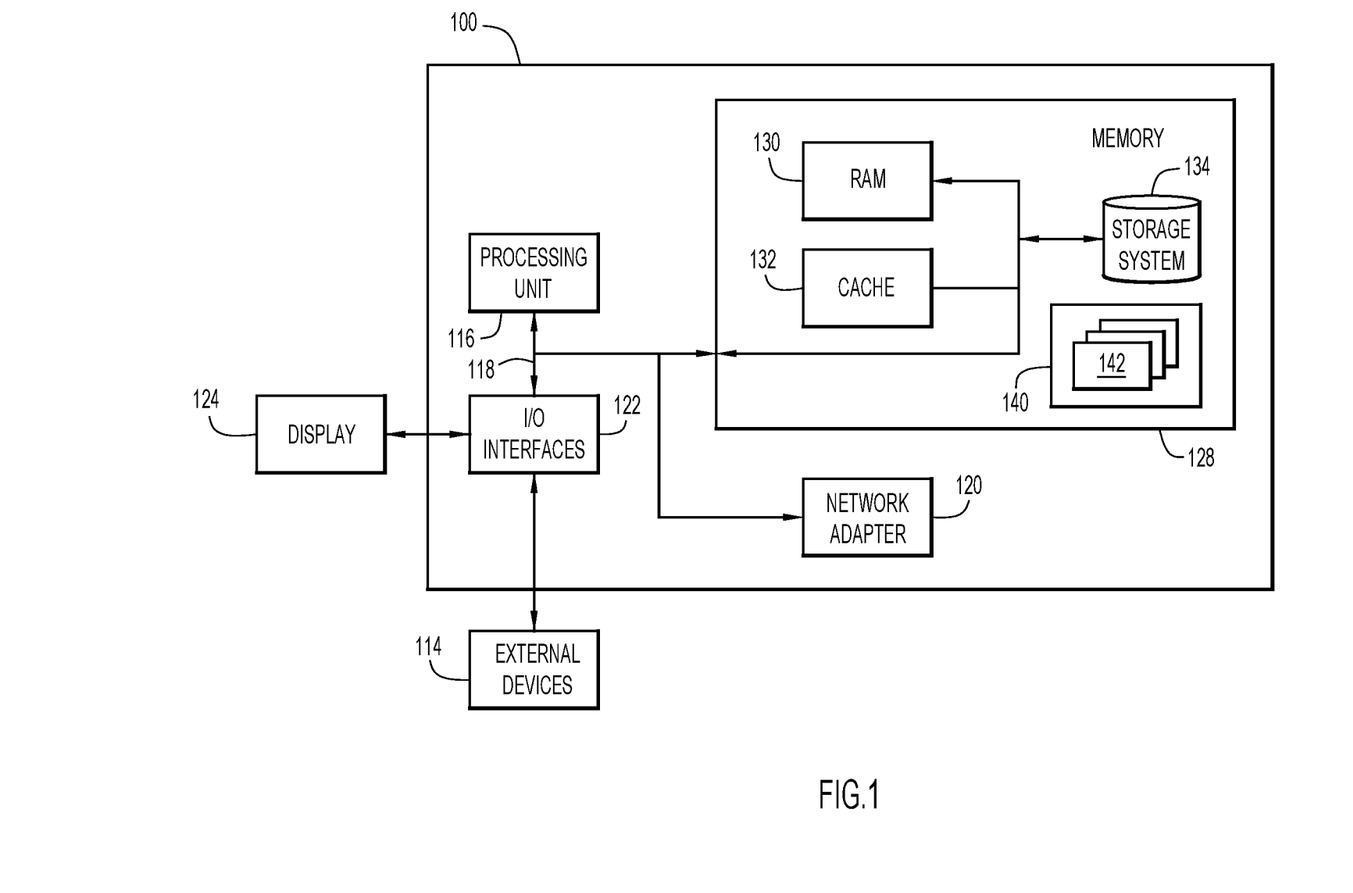
FIG. 1 illustrates a functional block diagram of an example computing system that can be used to implement various embodiments of the invention.

FIG. 1 is a functional block diagram of a computing system 100 that may implement various embodiments of the invention. Computing system 100 is shown in a form of a general-purpose computing device. Components of computing system 100 may include, but are not limited to, one or more processors or processing units 116, a system memory 128, and a bus 118 that couples various system components including system memory 128 to one or more processors 116.

Bus 118 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computing system 100 typically includes a variety of computer system readable media. Such media may be any available media that is accessible by computing system 100, and may include both volatile and non-volatile media, removable and non-removable media.

System memory 128 can include computer system readable media in the form of volatile memory, such as random access memory (RAM) 130 and/or cache memory 132. Computing system 100 may further include other removable/non-removable, volatile/non-volatile computer system storage media. By way of example only, storage system 134 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 118 by one or more data media interfaces. As will be further depicted and described below, memory 128 may include at least one program product having a set (e.g., at least one) of program modules that are configured to carry out the functions of embodiments of the invention.

Program/utility 140, having a set (at least one) of program modules 142, may be stored in memory 128 by way of example, and not limitation, as well as an operating system, one or more application programs, other program modules, and program data. Each of the operating system, the one or more application programs, the other program modules, and the program data or some combination thereof, may include an implementation of a networking environment. Program modules 142 generally carry out the functions and/or methodologies of embodiments of the invention as described herein.

Computing system 100 may also communicate with one or more external devices 114 such as a keyboard, a pointing device, a display 124, etc.; one or more devices that enable a user to interact with computing system 100; and/or any devices (e.g., network card, modem, etc.) that enable computing system 100 to communicate with one or more other computing devices. Such communication can occur via Input/Output (I/O) interfaces 122. Still yet, computing system 100 can communicate with one or more networks such as a local area network (LAN), a general wide area network (WAN), and/or a public network (e.g., the Internet) via network adapter 120. As depicted, network adapter 120 communicates with the other components of computing system 100 via bus 118. It should be understood that, although not shown, other hardware and/or software components could be used in conjunction with computing system 100. Examples, include, but are not limited to: microcode, device drivers, redundant processing units, external disk drive arrays, RAID systems, tape drives, and data archival storage systems, etc.

Figure 2:
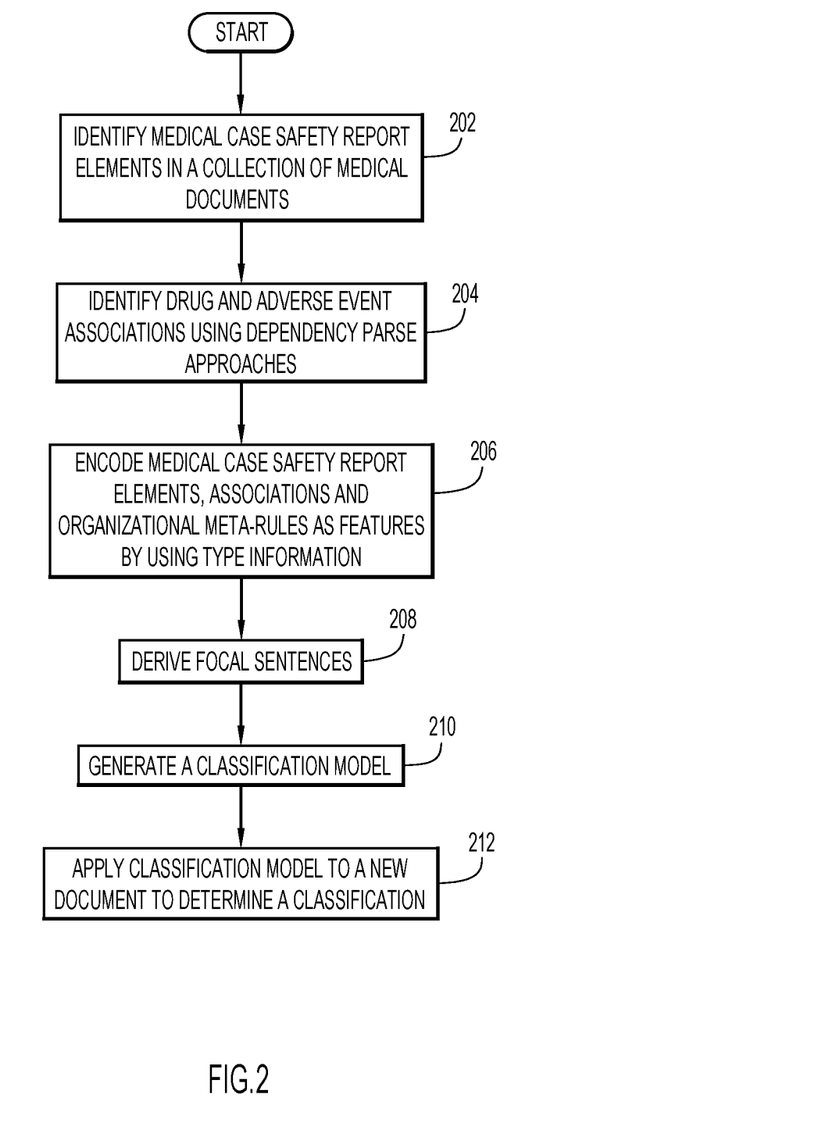
FIG. 2 is a flowchart of an example process for training, generating and applying a classification model to a document.

FIG. 2 is a flowchart that illustrates example processing that may be performed in various embodiments by a process executing on computing system 100. The process may begin by ingesting a corpus of homogeneous documents and performing a number of cognitive steps. A first cognitive step may include identifying one or more entities or elements within the corpus. The entities or elements may include patients, adverse events, reporters of the adverse events, and medical drugs (act 202).

Figure 3:
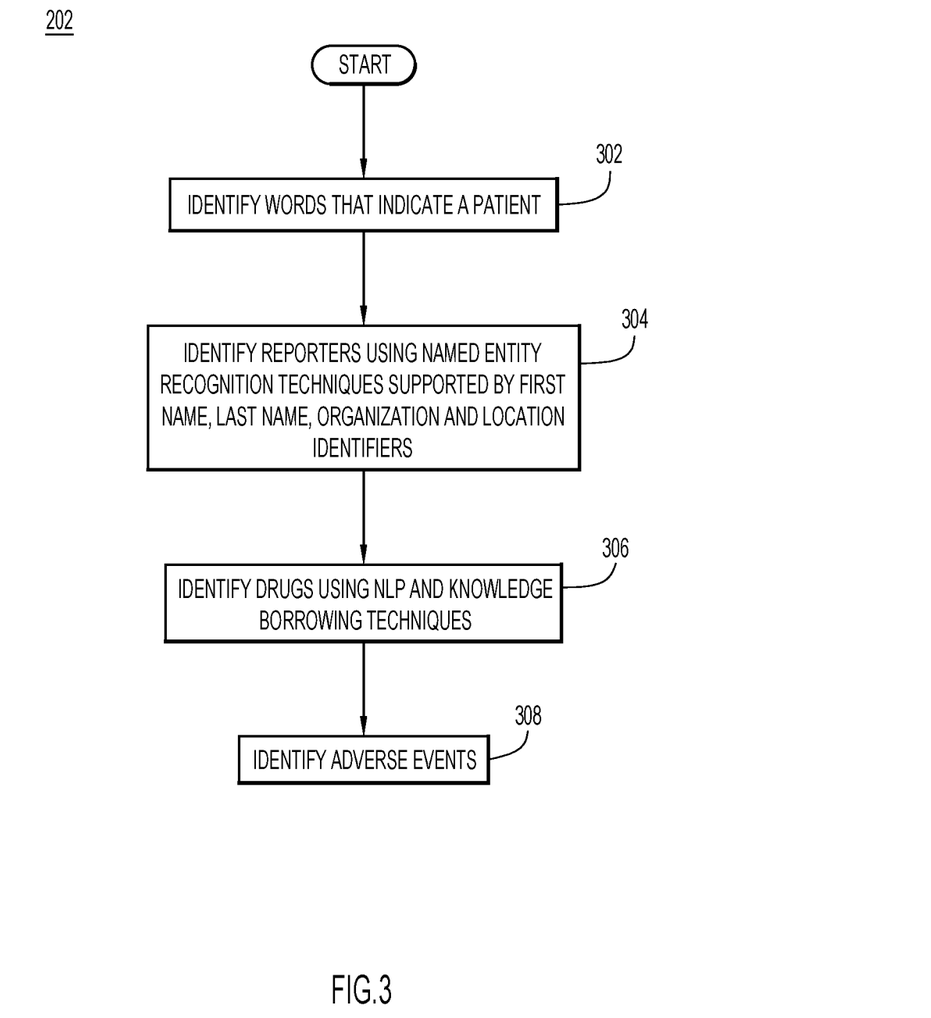
FIG. 3 is a more detailed flowchart of act 202 of FIG. 2 for identifying patients, reporters, drugs and adverse events in documents.

FIG. 3 is a flowchart of an example process for performing act 202. The process may begin by identifying words that indicate a patient (act 302). In some embodiments, any one of a number of methods may be used to identify words that indicate a patient. For example, embodiments may include a trained subsystem for identifying words that indicate a patient using natural language processing (NLP) and rule-based or other approaches. Other embodiments may start with an initial seed of only a few words that indicate a patient. The initial seed may include, for example, only five words in some embodiments. In other embodiments, another number of words may be included in the initial seed. Machine learning techniques such as, for example, semantic lexicon expansion may be used to identify a larger set of words for describing a patient in a representative corpus based on the initial seed. One example of a service that provides semantic lexicon expansion is Watson Concept Expansion by International Business Machines of Armonk, N.Y.

In embodiments that use semantic lexicon expansion, training data may be analyzed for words or phrases that appear before a word or a phrase indicating an entity and for words or phrases that appear after the word or the phrase indicating the entity to determine patterns. For example, assuming one or more known words and/or phrases that indicate a patient entity, embodiments may identify first words and/or first phrases that appear before the patient entity and may identify second words and/or second phrases that appear after the patient entity. Further, embodiments may identify first words and first phrases that appear before the entity and are used with particular ones of the second words and the second phrases appearing after the entity.

As an example, assume that training data is provided and known words that indicate a patient entity are, for example, male, female, patient, man or woman. In various embodiments, the words or phrases appearing before and after the patient entity may be analyzed such as, for example:

A 68 year old man with a history of . . .

A 23 year old woman treated with . . .

A frequency of use of each word or phrase appearing before or after the entity may be determined. Based on the training data, a score may be assigned to each word or phrase appearing before the entity and a score may be assigned to each word or phrase appearing after the entity. Such words or phrases may be assigned a high score based on the word or phrase having a high frequency of use with a particular type of entity such as, for example, the patient entity. In this way, embodiments may learn the words or phrases that precede or follow a particular type of entity. Similarly, these embodiments may learn words or phrases that precede or follow other types of entities such as a drug name, a reporter, and an adverse event.

As a result of analyzing the training data, each word or phrase appearing before or after a suspected entity may have a score associated with the suspected entity being identified as a particular type of entity such as, for example, a patient entity, a drug name entity, a reporter entity, and an adverse event entity. For example, according to the training data a phrase "A" appearing before an entity such as a patient entity may correctly indicate the patient entity 80% of the time, a phrase "B" appearing after the patient entity may correctly indicate the patient entity 90% of the time, and a combination of the phrase "A" appearing before the patient entity and the phrase "B" appearing after the patient entity may correctly indicate the patient entity 95% of the time. Thus, in the above example, a confidence score with respect to identifying an entity as a particular type of entity may be calculated as a combination of the score of each word or phrase that appears before and after a suspected entity based on a frequency of occurrence of the word or phrase being used with a suspected type of entity as indicated by the training data. As previously mentioned, the types of entities may include, but not be limited to, a patient entity, a drug name entity, an adverse event entity and a reporter entity.

Reporters may be identified by using machine learning and named entity recognition techniques (act 304). These techniques may be supported by first name, last name, organization and location identifiers. In some embodiments, semantic lexicon expansion techniques, as described above, may be used to learn words or phrases for identifying reporter entities. In other embodiments, a trained subsystem may be included for identifying reporters. Some embodiments may use other techniques for identifying reporters.

Drug names may be identified using natural language processing (NLP), knowledge borrowing techniques, semantic lexicon expansion techniques as well as other techniques (act 306). Knowledge borrowing (also known as inductive transfer learning) refers to a situation in which at least two datasets are sampled from distributions $p^P(x, y)$ and $p^S(x, y)$, and in general, $p^P(x, y) \neq p^S(x, y)$. Typically, a number of the P data is much smaller than a number of the S data. Further, because of the small number of the P data, a model learned solely on the P data usually does not provide good quality predictions. However, an assumption is made that the distributions $p^P$ and $p^S$ are similar to some degree. Using knowledge borrowing techniques, one may achieve good prediction quality by using the S data. In some embodiments, a trained subsystem may be included for identifying drug names.

Next, an adverse event entity may be identified using any of a number of new or existing techniques (act 308). For example, some embodiments may employ semantic lexicon expansion techniques, as previously described, to identify suspected adverse event entities. In some embodiments, adverse event entities may be identified by using a machine learning based sequential labeling technique.

Sequential labeling is a type of pattern recognition task that involves algorithmic assignment of a categorical label to each member of a sequence of observed values. Part of speech tagging is one common example of a machine learning sequential labeling task, which includes assigning of a part of speech to each word in an input sentence or document. Machine learning sequential labeling can be treated as a set of independent classification tasks, one per member of the sequence. Accuracy may be improved by making an optimal label for a given element dependent on choices for nearby elements, using special algorithms to choose a globally best set of labels for an entire sequence at once. Most machine learning based sequential labeling algorithms are probabilistic in nature and rely on statistical inference to find a best sequence. Common statistical models for machine learning based sequential labeling make a Markov assumption. That is, a label chosen for a particular word is directly dependent only on immediately adjacent labels. Thus, the set of labels forms a Markov chain, which leads naturally to a hidden Markov model (HMM), which is one of the most common statistical models used for machine learning based sequential labeling. Other common models may include a maximum entropy Markov model and a conditional random field.

Various embodiments may include an annotator for annotating identified elements or entities. In some embodiments, the identified entities may be annotated with a name of a type of the recognized entity including, but not limited to, for example, patient, drug (or drug name), reporter and adverse event.

Returning to FIG. 2, drug and adverse event associations may be identified using any of a number of techniques (act 204). In some embodiments, dependency parse approaches may be employed to identify an association between a drug and an adverse event. For example, a patient can be administered multiple drugs. An adverse event may not be caused by company X's drug, but may be caused by a drug of a competitor, company Y. In this example, a medical case safety report would be classified as invalid for company X. To draw correct associations, embodiments search for clear connections between entities and adverse events using a NLP dependency parse tree. The associations may include a patient/drug connection, a drug/adverse-event connection and a patient/adverse event connection. All of these are rarely mentioned in a single sentence. By extracting pairwise associations, these features can be combined in a probabilistic model to inform a medical case safety report decision.

Figure 4:
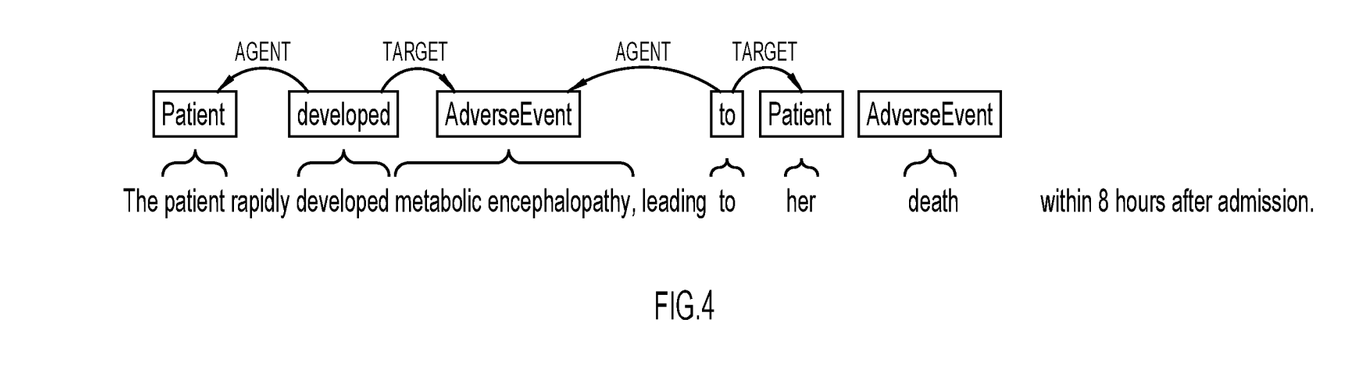
FIG. 4 illustrates example dependency parsing of a sentence, which identifies a patient, an adverse event, and an association between the patient and the adverse event.

FIG. 4 illustrates an example of a dependency parse tree in which semantic role labeling may be used to determine a connection between a patient and an adverse event. In this example, the sentence "The patient rapidly developed metabolic encephalopathy leading to her death within 18 hours after admission." is parsed. A verb, "developed" is found having an agent "patient", which may be identified as a patient entity, and a target "metabolic encephalopathy", which may be identified as an adverse event entity. Next, a connector "to", which is a preposition, is found, which has the adverse event "metabolic encephalopathy" identified as an agent and the word "her" identified as a target and labeled as a patient. The word "death" may be labeled as an adverse event entity. As a result, a clear connection is found between a female patient and the adverse event "metabolic encephalopathy".

Figure 5:
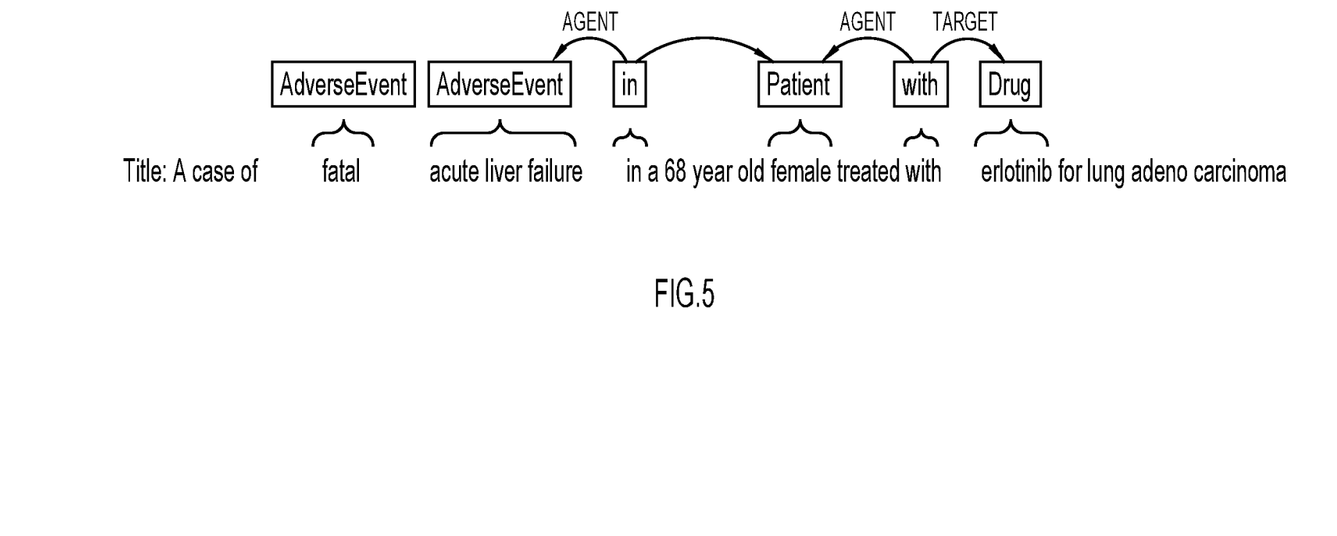
FIG. 5 illustrates another example of dependency parsing for identifying a patient, an adverse event, a drug, and associations between the patient and the adverse event, the patient and the drug, and the drug and the adverse event.

FIG. 5 illustrates a second example of a dependency parse tree in which semantic role labeling may be used to determine a connection between a patient treated with a drug and an adverse event. In this example, a string "Title: A case of fatal acute liver failure in a 68 year old female treated with erlotinib for lung adenocarcinoma" is parsed. The words "fatal" and "acute liver failure" may be labeled as adverse events. A connector "in", which is a preposition, may be identified as having the adverse event "acute liver failure" as an agent and female, labeled as a patient entity, as a target. The word "with", which is identified as a connector, has a patient entity "female" as an agent. The word "erlotinib" is labeled as a drug entity, which is identified as a target of the connector "with". As a result, a clear connection is found between the patient "female" and the adverse events "fatal" and "acute liver failure", a clear connection is found between the patient "female" and the drug "erlotinib", and a clear connection is found between the adverse events "fatal" and "acute liver failure" and the drug "erlotinib".

In some embodiments, a dependency parse tree based on part of speech tagging is used to determine associations between a patient and a drug, a drug and an adverse event, and a patient and an adverse event.

Returning to FIG. 2, medical case safety report elements, associations and organizational meta-rules may be encoded as features by using type information (act 206). Encoding types such as, for example, entity types, causality types and meta-rules, results in better machine learning of abstractions. Table 1 shows an example of encoded features and their corresponding text, some of which can be found in FIGS. 4 and 5.

Various embodiments may keep track of offsets of entities or features found in a document. The entities or features may be presented as evidence of a feature or entity found in the document. Table 1, shown below, illustrates various features with corresponding evidence found in a document. The features may be automatically encoded based on results of machine learning and also may be manually encoded in some embodiments.

TABLE 1

| Evidence Found in Document | Feature Encoded |
|---|---|
| Erlotnib | Suspect Drug |
| Fatal Acute Liver Failure | Adverse Event |
| Pregnant Patient | Pregnancy Meta-rule |
| Verb: Developed | Patient Event Link |
| Agent: Patient | |
| Target: Metabolic Encephalopathy | |

In some embodiments, at least one organizational meta-rule may be encoded as a feature. For example, a company causality meta-rule may be encoded for filtering out and ignoring names of drugs not in a pharmaceutical company's portfolio. In other embodiments, some features such as, for example, the company causality meta-rule, may be implemented via a post-processing step. In such other embodiments, an identified suspected drug may be checked against a drug company's portfolio and may be ignored if the drug is not included in the portfolio.

Focal sentences may then be derived (act 208). The focal sentences for a document are a subset of sentences in the document that include drug, adverse event and causality cues. FIG. 6 shows example text of a document. In the document, various entities or features may have been identified by an embodiment. Some embodiments may highlight the identified entities or features to point out the identified entities or features. Various embodiments may identify types of the identified entities via various techniques including, but not limited to, using specific colors to highlight specific types of identified entities (not shown). In some embodiments, focal sentences may be highlighted as illustrated in FIG. 6.

Various embodiments may generate a learned binary classification model using the encoded features and cues included in focal sentences (act 210) during a training phase. The binary classification model may be applied to new documents to classify each of the new documents as being either a valid medical case safety report or an invalid medical case safety report (act 212).

In some embodiments, a confidence score may be determined. The confidence score may indicate a level of confidence regarding accuracy of a classification of a document. In such embodiments, a frequency of use of each word or phrase appearing before or after a suspected entity is determined. Based on training data, a score may be assigned to each of the words or phrases appearing before the suspected entity and a score may be assigned to each of the words or phrases appearing after the suspected entity. Such words or phrases may be assigned a high score based on the word or phrase having a high frequency of use with a type of entity and may be assigned a low score based on the word or phrase having a low frequency of use with a type of entity. The scores of the words or phrases appearing before and after the suspected entity may be combined to produce a confidence score for a type of the suspected entity. The suspected entity may then be identified as an entity of a particular type based on the produced confidence score. As an example, a suspected entity may be identified as a patient entity type with a confidence score of 90%, indicating a high likelihood that the suspected entity is correctly identified as the patient entity type. Some embodiments may identify types of various entities only if a corresponding score, with respect to correctly identifying a type of the entity, is greater than or equal to a minimum threshold value, which may be 50%, 60%, or another suitable value. In some embodiments, a confidence score of a classification of a document as being valid may be based on a number of identified features or entities that are indicative of a medical case safety report.

Various embodiments executing in a prediction mode and using the generated binary classification model may produce output with respect to a previously unseen document. The following is an example output that may be produced for a document by some embodiments:

DocID: 126273
Decision: ICSR Valid
Confidence: 60%
Evidence showing 4 detected medical case safety report elements and focal sentences.

The environment of present invention embodiments may include any number of computers or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and may communicate via any suitable communications medium (e.g., LAN, WAN, Intranet, Internet, hardwired, modem connection, wireless, etc.). For example, the functions of the present invention embodiments may be distributed in any manner among the various systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to a server and/or client systems. The database systems and/or storage structures may be remote from or local to the computer or other processing systems, and may store any desired data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A method for generating and applying a learned classification model to determine a classification of documents, the method comprising:

identifying, by a computing system using one or more machine-learning trained subsystems, one or more words indicating a patient, a reporter, and one or more adverse events within a document, the identifying the one or more words indicating the patient further comprising:

identifying the one or more words indicating the patient based on semantic lexicon expansion of an initial group of terms occurring during a training phase and comprising:

analyzing training data for one of a first word and a first phrase appearing before one of any word and any phrase known to indicate the patient entity, and for one of a second word and a second phrase appearing after the one of the any word and the any phrase to determine a first frequency of occurrence of the one of the first word and the first phrase appearing before the one of the any word and the any phrase and to determine a second frequency of occurrence of the one of the second word and the second phrase appearing after the one of the any word or the any phrase, and calculating a first confidence score for the one of the first word and the first phrase appearing before the one of the any word and the any phrase and a second confidence score for the one of the second word and the second phrase appearing after the one of the any word and the any phrase based on the first frequency of occurrence and the second frequency of occurrence;

identifying, by the computing system, one or more medical drug names in the document using natural language processing;

analyzing, by the computing system, the document to determine associations between the patient and a medical drug, the medical drug and an adverse event, and the patient and the adverse event;

determining features, by the computing system, based on type information corresponding to the identified patient, the identified reporter, the identified one or more medical drug names, the identified one or more adverse events, and the determined associations;

identifying, by the computing system, elements of a medical case safety report based on the identified one or more words indicating the patient, the reporter, and the one or more adverse events within the document;

generating, by the computing system, the learned classification model based at least on the determined features and the identified elements of the medical case safety report during the training phase to identify medical case safety reports within the documents; and applying, by the computing system, the learned classification model to a new document to determine a classification of the new document as one of a valid medical case safety report and an invalid medical case safety report.

2. The method of claim 1, further comprising:
identifying the one or more words indicating the reporter based on named entity recognition techniques; and
identifying the one or more medical drug names based on using the natural language processing and knowledge borrowing techniques.

3. The method of claim 1, wherein the analyzing of the document to determine the associations comprises:
determining the association between the medical drug and the adverse event based on a natural language processing dependency parse tree.

4. The method of claim 1, further comprising:
determining a confidence score for the determined classification of the classification model.

5. The method of claim 1, wherein the generating the learned classification model comprises:
generating the learned classification model based on the determined features and linguistic features associated with identified portions of documents including the elements of the medical case safety report including a patient, a reporter, a medical drug name, and an adverse event.

6. The method of claim 1, wherein the new document includes one of a safety report, a clinical trial report, a legal document, a social media document, and a scientific literature document.

7. The method of claim 1, wherein the determined features include at least one organizational meta-rule.

8. A computing system for generating and applying a learned classification model to determine a classification of documents, the computing system comprising:
at least one computing device, each of the at least one computing device comprising:
at least one processor;
a memory; and
a communication bus connecting the at least one processor with the memory; and
wherein the at least one processor is configured to perform:
identifying, using a first machine-learning trained subsystem, one or more words indicating a patient, a reporter, and one or more adverse events within a document, the identifying the one or more words indicating the patient further comprising:
identifying the one or more words indicating the patient based on semantic lexicon expansion of an initial group of terms, the semantic lexicon expansion of the initial group of terms occurring during a training phase and comprising:
analyzing training data for one of a first word and a first phrase appearing before one of any word and any phrase known to indicate the patient entity, and for one of a second word and a second phrase appearing after the one of the any word and the any phrase to determine a first frequency of occurrence of the one of the first word and the first phrase appearing before the one of the any word and the any phrase and to determine a second frequency of occurrence of the one of the second word and the second phrase appearing after the one of the any word or the any phrase, and
calculating a first confidence score for the one of the first word and the first phrase appearing before the one of any word and the any phrase and a second confidence score for the one of the second word and the second phrase appearing after the one of the any word and the any phrase based on the first frequency of occurrence and the second frequency of occurrence;

identifying one or more medical drug names in the document using natural language processing;

analyzing the document to determine associations between the patient and a medical drug, the medical drug and an adverse event, and the patient and the adverse event;

determining features based on type information corresponding to the identified patient, the identified reporter, the identified one or more drug names, the identified one or more adverse events, and the determined associations;

identifying elements of a medical case safety report based on the identified one or more words indicating the patient, the reporter, and the one or more adverse events within the document;

generating the learned classification model based at least on the determined features and the identified elements of the medical case safety report during the training phase to identify medical case safety reports within the documents; and applying the learned classification model to a new document to determine a classification of the new document as one of a valid medical case safety report and an invalid medical case safety report.

9. The computing system of claim 8, wherein the at least one processor is further configured to perform:
identifying the one or more words indicating the reporter based on named entity recognition techniques; and
identifying the one or more medical drug names based on using the natural language processing and knowledge borrowing techniques.

10. The computing system of claim 8, wherein the analyzing of the document to determine the associations comprises:
determining the association between the medical drug and the adverse event based on a natural language processing dependency parse tree.

11. The computing system of claim 8, wherein the at least one processor is further configured to perform:
determining a confidence score for the determined classification of the classification model.

12. The computing system of claim 8, wherein the generating the learned classification model comprises:
generating the learned classification model based on the determined features and linguistic features associated with identified portions of documents including the elements of a medical case safety report, the elements of the medical case safety report including the patient, the reporter, the medical drug name, and the adverse event.

13. The computing system of claim 8, wherein the new document includes one of a safety report, a clinical trial report, a legal document, a social media document, and a scientific literature document.

14. The computing system of claim 8, wherein the determined features include at least one organizational meta-rule.

15. A computer program product comprising:
   at least one non-transitory computer readable storage medium having computer readable program code embodied therewith for execution on at least one processor, the computer readable program code being configured to be executed by the at least one processor to perform:
      identifying, using one or more machine-learning trained subsystems, one or more words indicating a patient, a reporter, and one or more adverse events within a document, the identifying the one or more words indicating the patient further comprising:
         identifying the one or more words indicating the patient based on semantic lexicon expansion of an initial group of terms, the semantic lexicon expansion of the initial group of terms occurring during a training phase and comprising:
            analyzing training data for one of a first word and a first phrase appearing before one of any word and any phrase known to indicate the patient entity, and for one of a second word and a second phrase appearing after the one of the any word and the any phrase to determine a first frequency of occurrence of the one of the first word and the first phrase appearing before the one of the any word and the any phrase and to determine a second frequency of occurrence of the one of the second word and the second phrase appearing after the one of the any word or the any phrase, and
            calculating a first confidence score for the one of the first word and the first phrase appearing before the one of the any word and the any phrase and a second confidence score for the one of the second word and the second phrase appearing after the one of the any word and the any phrase based on the first frequency of occurrence and the second frequency of occurrence;
      identifying one or more medical drug names in the document using natural language processing;
      analyzing the document to determine associations between the patient and a medical drug, the medical drug and an adverse event, and the patient and the adverse event;
      determining features based on type information corresponding to the identified patient, the identified reporter, the identified one or more drug names, the identified one or more adverse events, and the determined associations;
      identifying elements of a medical case safety report based on the identified one or more words indicating the patient, the reporter, and the one or more adverse events within the document;
      generating a learned classification model based at least on the determined features and the identified elements of the medical case safety report during the training phase to identify medical case safety reports within medical documents; and
      applying the learned classification model to a new document to determine a classification of the new document as one of a valid medical case safety report and an invalid medical case safety report.

16. The computer program product of claim 15, wherein the computer readable program code is configured to be executed by the at least one processor to perform:
   identifying the one or more words indicating the reporter based on named entity recognition techniques; and
   identifying the one or more medical drug names based on using the natural language processing and knowledge borrowing techniques.

17. The computer program product of claim 15, wherein the analyzing of the document to determine the associations comprises:
   determining the association between the medical drug and the adverse event based on a natural language processing dependency parse tree.

18. The computer program product of claim 15, wherein the computer readable program code is further configured to be executed by the at least one processor to perform:
   determining a confidence score for the determined classification of the classification model.

19. The computer program product of claim 15, wherein the generating the learned classification model comprises:
   generating the learned classification model based on the determined features and linguistic features associated with identified portions of documents including the elements of a medical case safety report, the elements of the medical case safety report including the patient, the reporter, the medical drug name, and the adverse event.

20. The computer program product of claim 15, wherein the new document includes one of a safety report, a clinical trial report, a legal document, a social media document, and a scientific literature document.

21. The computer program product of claim 15, wherein the determined features include at least one organizational meta-rule.

* * * * *